(12) United States Patent
Chujo et al.

(10) Patent No.: US 8,299,283 B2
(45) Date of Patent: Oct. 30, 2012

(54) CONTRAST AGENT CONTAINING SILSESQUIOXANE

(75) Inventors: Yoshiki Chujo, Kyoto (JP); Kazuo Tanaka, Kyoto (JP); Kensuke Naka, Kyoto (JP)

(73) Assignee: Kyoto University, Kyoto (JP)

( * ) Notice: Subject to any disclaimer, the term of this patent is extended or adjusted under 35 U.S.C. 154(b) by 268 days.

(21) Appl. No.: 12/733,464
(22) PCT Filed: Sep. 3, 2008
(86) PCT No.: PCT/JP2008/065905
§ 371 (c)(1), (2), (4) Date: Mar. 3, 2010
(87) PCT Pub. No.: WO2009/031593
PCT Pub. Date: Mar. 12, 2009

(65) Prior Publication Data
US 2010/0256404 A1 Oct. 7, 2010

(30) Foreign Application Priority Data
Sep. 3, 2007 (JP) .................................. 2007-228382

(51) Int. Cl.
*C07F 7/18* (2006.01)
*C07F 7/00* (2006.01)
(52) U.S. Cl. ............................. 556/9; 556/460; 534/15
(58) Field of Classification Search ................. 556/460, 556/9; 534/15
See application file for complete search history.

(56) References Cited

U.S. PATENT DOCUMENTS
6,372,194 B1 4/2002 Akaike et al.
2006/0166135 A1 7/2006 Wada FOREIGN PATENT DOCUMENTS
JP 2000-86538 3/2000
(Continued)

OTHER PUBLICATIONS
Feher et al., Chem. Commun., (3), pp. 323-324 (1998).*
(Continued)

*Primary Examiner* — Porfirio Nazario Gonzalez
(74) *Attorney, Agent, or Firm* — Wenderoth, Lind & Ponack, L.L.P.

(57) ABSTRACT

The present invention provides a contrast agent which ensures 1) high contrast performance, 2) low toxicity, and 3) a simple production process.
The present invention provides a contrast agent containing a silsesquioxane represented by General Formula (I),

[Chem. 1]

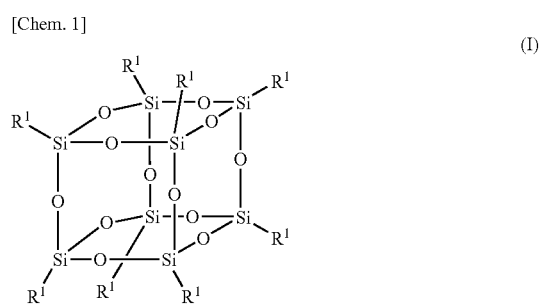

(I)

wherein $R^1$, the same or different, is a substituent bonded to Si through a carbon atom, the substituent having, at its terminal, a group represented by General Formula (II),

[Chem. 2]

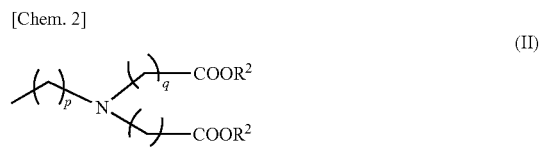

(II)

wherein p represents an integer of from 1 to 5; q is the same or different, and represents an integer of from 1 to 5; $R^2$ is the same or different, and represents hydrogen atom, alkyl group, aralkyl group or acyl group,
or a group represented by General Formula (III),

[Chem. 3]

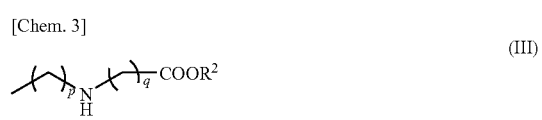

(III)

wherein p, q and $R^2$ are the same as above.

15 Claims, 2 Drawing Sheets

FOREIGN PATENT DOCUMENTS

| | | |
|---|---|---|
| JP | 2006-201711 | 8/2006 |
| WO | 98/41241 | 9/1998 |

OTHER PUBLICATIONS

International Search Report issued Oct. 21, 2008 in International (PCT) Application No. PCT/JP2008/065905.

Kensuke Naka et al., "Water-Soluble Anionic POSS-Core Dendrimer: Synthesis and Copper(II) Complexes in Aqueous Solution", Langmuir, vol. 23, No. 17, pp. 9057-9063, Aug. 14, 2007.

Frank J. Feher et al., "Syntheses of highly functionalized cube-octameric polyhedral oligosilsesquioxanes $(R_8Si_8O_{12})$", J. Chem. Soc., Dalton Trans., vol. 9, pp. 1491-1497, 1999.

Frank J. Feher et al., "Amine and ester-substituted silsesquioxanes: synthesis, characterization and use as a core for starburst dendrimers", Chem Commun., vol. 3, pp. 323-324, 1998.

Hongzhi Liu et al., "Montmorillonite intercalated by ammonium of octaaminopropyl polyhedral oligomeric silsesquioxane and its nanocomposites with epoxy resin", Polymer, vol. 46, pp. 157-165, 2005.

Supplementary European Search Report issued Jun. 22, 2012 in corresponding European Application No. 08829487.1.

Corr et al., "Magnetic-fluorescent nanocomposites for biomedical multitasking", Chemical Communications, No. 43, Jan. 1, 2006, pp. 4474-4476.

* cited by examiner

DTPA
DOTA
PAMAMdendrimer

CONTRAST AGENT CONTAINING SILSESQUIOXANE

TECHNICAL FIELD

The present invention relates to a contrast agent containing a silsesquioxane, and a process for producing the silsesquioxane.

BACKGROUND ART

Various diagnostic imaging methods, such as X-ray CT (computed tomography), ultrasound imaging, MRI (magnetic resonance imaging) diagnosis, scintigraphy, etc. now exist. MRI is particularly advantageous because it can produce, without fear of exposure, cross-sectional images of body parts such as the brain, spinal cord, etc., where imaging by X-ray CT is often very difficult.

With MRI diagnosis, images are synthesized by computer based on signal data from hydrogen nuclei in the body so as to examine the condition of organs. Accordingly, MRI diagnosis is performed using paramagnetic metal ions having properties that shorten the relaxation time by interacting with nearby hydrogen nuclei. Among such metal ions, $Gd^{3+}$ is particularly excellent in terms of the above-described properties, and increases the intensity of the signals in T1 weighted images. However, metal ions such as $Gd^{3+}$ and the like are highly toxic, and therefore are stabilized by being bonded to a chelating ligand before being used as contrast agents for MRI.

Conventionally, diethylenetriamine pentaacetic acid (DTPA), 1,4,7,10-tetraazacyclododecane-1,4,7,10-tetraacetate (DOTA) and the like, which have an affinity with $Gd^{3+}$, have been used as the chelating agent.

For example, Patent Document 1 discloses a contrast agent for MRI containing a complex between a polyanionic gadolinium (Gd)-based contrast agent and a cationic polymer, or a complex between a polycationic Gd-based contrast agent and an anionic polymer; these complexes are able to form a polyion complex, wherein the contrast agent can produce MRI contrast only in the presence of polyelectrolyte in the neutral pH range.

Further, Patent Document 2 discloses a contrast agent comprising a complex between a gadolinium (Gd)-based contrast agent and a polymer, wherein the polymer undergoes a phase change in response to environmental changes, and thereby changes the water solubility.

Another Gd complex, as shown in FIG. 1, has also been reported. This Gd complex is formed by coordination of a dendrimer to $Gd^{3+}$, the dendrimer being formed by the reaction of DTPA or DOTA with $NH_3^+$ groups at the terminals of polyamidoamine (PAMAM) dendrimer.

However, a metal complex having DTPA or DOTA as the chelating ligand has low contrast performance. In other words, the sensitivity to detect target cells such as tumors and the like is low. Accordingly, when a contrast agent that contains the above-described complex as the essential component is used, the concentration of the complex in the contrast agent must be high. Such a high concentration of the contrast agent poses a problem, i.e., the risk of adverse effects with the use of the contract agent is high.

Further, there is a demand for an MRI diagnosis that can be performed in the future using a high magnetic field, in order to obtain a higher resolution. However, the contrast performance of the above-mentioned metal complexes is reduced in high magnetic fields, thus making it difficult to use them for MRI diagnosis in a high magnetic field. Further, because the molecular weights of DTPA and DOTA are low, the complexes tend to diffuse in the body, thus causing images to become blurred easily. In other words, the use of a complex between DTPA or DOTA and Gd poses problematically low resolution in diagnostic images.

Further, the use of Gd complex to which DTPA or DOTA is coordinated tends to cause $Gd^{3+}$ to be dissociated from the complex. Accordingly, a contrast agent that uses the complex is highly toxic.

Further, the Gd complex is highly mobile (molecular rotation easily occurs). This can reduce the contrast performance.

Note that, although the Gd complex shown in FIG. 1 is excellent in terms of the contrast performance and the like, it is difficult to synthesize.

[Patent Document 1] WO98/41241
[Patent Document 2] Japanese Unexamined Patent Publication No. 2000-86538

DISCLOSURE OF THE INVENTION

Technical Problem

A main object of the present invention is to provide a contrast agent having 1) high contrast performance, 2) low toxicity, and 3) a simple production process.

Technical Solution

The present inventors conducted intensive research. As a result, they found that the above-described object can be achieved by a contrast agent containing a specific silsesquioxane and a specific production process for producing the silsesquioxane, and completed the present invention.

Specifically, the present invention relates to a contrast agent, a silsesquioxane, and a method for producing the silsesquioxane described below.

1. A contrast agent containing a silsesquioxane represented by General Formula (I),

[Chem. 1]

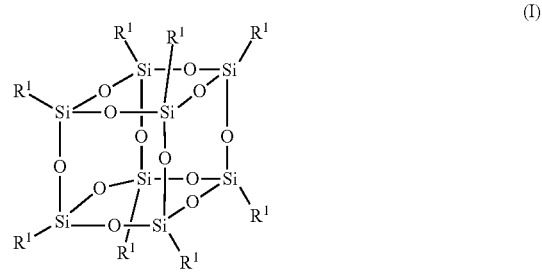

wherein $R^1$, the same or different, is a substituent bonded to Si through a carbon atom, the substituent having, at its terminal, a group represented by General Formula (II),

[Chem. 2]

wherein p represents an integer of from 1 to 5; q is the same or different, and represents an integer of from 1 to 5; $R^2$ is the same or different, and represents hydrogen atom, alkyl group, aralkyl group or acyl group, or a group represented by General Formula (III),

[Chem. 3]

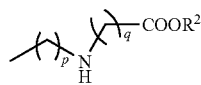
(III)

wherein p, q and $R^2$ are the same as above.

Silsesquioxane

The contrast agent of the present invention contains a silsesquioxane represented by General Formula (I)

[Chem. 4]

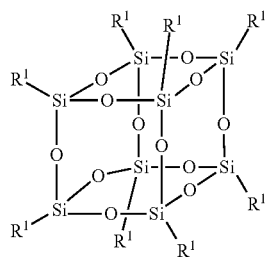
(I)

wherein each $R^1$, the same or different, is a substituent bonded to Si through a carbon atom, the substituent having, at its terminal, a group represented by General Formula (II),

[Chem. 5]

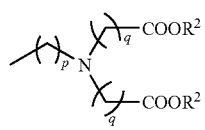
(II)

wherein p represents an integer of from 1 to 5, preferably an integer of from 2 to 4; each q is the same or different, and represents an integer of from 1 to 5, preferably an integer of 1 or 2; and each $R^2$ is the same or different, and represents hydrogen atom, alkyl group, aralkyl group, or acyl group, or a group represented by General Formula (III)

[Chem. 6]

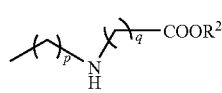
(III)

wherein p, q, and $R^2$ are as defined above.

The contrast agent of the present invention contains a metal complex. The contrast agent of the present invention contains the silsesquioxane as a ligand coordinated to a metal ion of the complex, thereby providing a contrast agent having high contrast performance and low toxicity.

The metal ion is preferably a paramagnetic metal ion, more preferably $Gd^{3+}$.

Examples of the alkyl group include methyl, ethyl, isopropyl, etc.

Examples of the aralkyl group include benzyl, naphthylmethyl, phenylethyl, etc.

Examples of the acyl group include formyl, acetyl, propionyl, cyclopentylcarbonyl, benzoyl, etc.

In particular, $R^2$ is preferably a hydrogen atom. When $R^2$ is a hydrogen atom, the silsesquioxane can be more suitably coordinated to the metal ion. A silsesquioxane wherein $R^2$ is a hydrogen atom can be easily produced by deprotecting, for example, a silsesquioxane wherein the $R^2$ is an alkyl group, an aralkyl group, an acyl group, or the like.

The silsesquioxane has a structure in which the nucleus is a cube structure formed from Si and O as shown in General Formula (I), and each substituent $R^1$ having a group represented by General Formula (II) or (III) at its terminal is dendritically projecting from the nucleus. In other words, the silsesquioxane is a so-called dendrimer polymer. In particular, between General Formulae (II) and (III), the above-described substituent $R^1$ preferably has a group represented by General Formula (II), in terms of the fact that such a group can be suitably coordinated to a metal ion.

In General Formula (1), 8 $R^1$ moieties are bonded to the cube structure; however, any of these 8 $R^1$ moieties may not be present insofar as the effect of the present invention is not adversely affected. It is particularly preferred that 8 $R^1$ moieties are bonded as shown in General Formula (I) in terms of facilitating coordination to a metal ion. Preferably, each $R^1$ described above is the same in view of easy production; however, some of them may be modified by functional molecules having fluorescence properties and the PET ability.

The silsesquioxane is not limited insofar as its substituent $R^1$ has a group represented by General Formula (II) or (III) at its terminal.

Examples thereof include a silsesquioxane (hereinafter sometimes referred to as "silsesquioxane A") wherein the $R^1$ in General Formula (I) is a substituent represented by General Formula (IIA)

[Chem. 7]

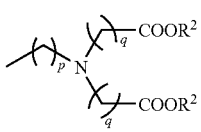
(IIA)

wherein p, q, and $R^2$ are as defined above, or by General Formula (IIIA)

[Chem. 8]

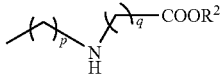
(IIIA)

wherein p, q, and $R^2$ are as defined above.

In the present specification, the silsesquioxane A is defined as a silsesquioxane whose generation number n is 1 (first generation).

Preferably, the p is an integer of from 2 to 4.
Preferably, the q is an integer of 1 or 2.
Preferably, the $R^2$ is a hydrogen atom.

In particular, between General Formulae (IIA) and (IIIA), the above-described $R^1$ is preferably a substituent represented by General Formula (IIA).

The silsesquioxane A can be coordinated to up to 2 metal ions, as shown in FIG. 2. Note that FIG. 2 shows the coordination of a silsesquioxane, as an example of the silsesquioxane A, wherein the $R^1$ in General Formula (I) is a substituent represented by General Formula (IIA), wherein p=3, q=1, and $R^2$=H.

The generation number n of the silsesquioxane is not limited insofar as the effect of the present invention is not adversely affected. The generation number n is usually 10 or less, preferably 1 to 3.

Examples of a silsesquioxane whose generation number n is 2 (second generation) include a silsesquioxane (hereinafter sometimes referred to as "silsesquioxane B") wherein the $R^1$ is a substituent represented by General Formula (IIB)

[Chem. 9]

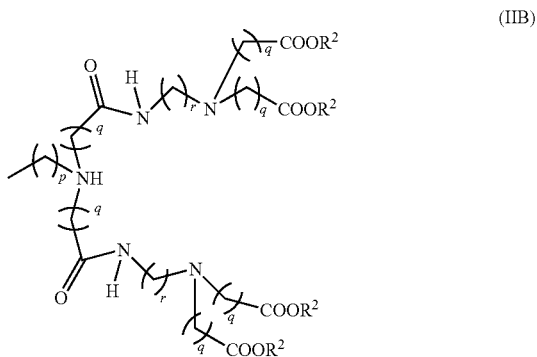

(IIB)

wherein p, q, and $R^2$ are as defined above, and r represents an integer of from 2 to 10.

Preferably, the p is an integer of from 2 to 4.

Preferably, the q is an integer of 1 or 2.

Preferably, the r is an integer of from 2 to 4.

Preferably, the $R^2$ is a hydrogen atom.

The silsesquioxane B can be coordinated to up to 4 metal ions.

Examples of a silsesquioxane whose generation number n is 3 (third generation) include a silsesquioxane (hereinafter sometimes referred to as "silsesquioxane C") wherein the $R^1$ is a substituent represented by General Formula (IIC)

[Chem. 10]

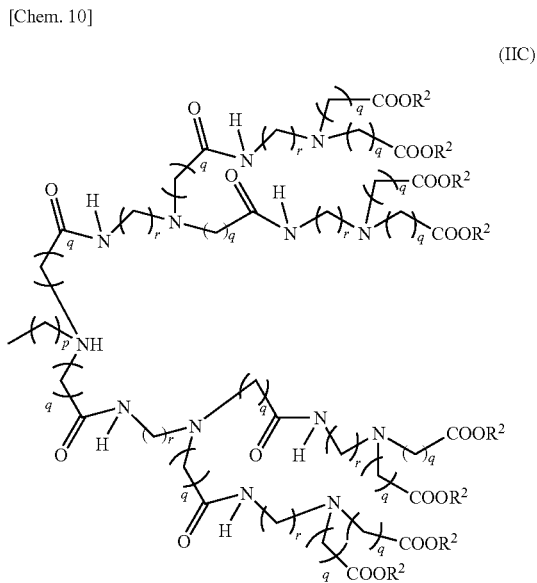

(IIC)

wherein p, q, r, and $R^2$ are as defined above.

Preferably, the p is an integer of from 2 to 4.

Preferably, the q is an integer of 1 or 2.

Preferably, the r is an integer of from 2 to 4.

Preferably, the $R^2$ is a hydrogen atom.

The silsesquioxane C can be coordinated to up to 8 metal ions.

The description below shows a particularly preferred embodiment among the silsesquioxanes described above.

Preferred Embodiment of the Silsesquioxane

A particularly preferred embodiment among the silsesquioxanes described above is one represented by General Formula (Ia)

[Chem. 11]

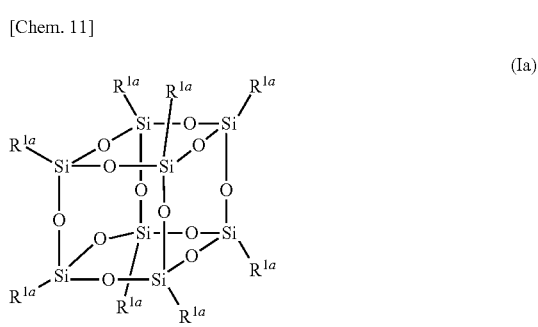

(Ia)

wherein each $R^{1a}$, the same or different, is a substituent bonded to Si through a carbon atom, the substituent having $-N(-CH_2-COOH)_2$ or $-NH-CH_2-COOH$ at its terminal.

Each substituent $R^{1a}$ of the silsesquioxane has, at its terminal, $-N(-CH_2-COOH)_2$ or $-NH-CH_2-COOH$, preferably $-N(-CH_2-COOH)_2$.

Preferably, each $R^{1a}$ described above is the same in view of easy production.

Examples thereof include a silsesquioxane (hereinafter sometimes referred to as "silsesquioxane a") whose generation number n is 1, wherein the $R^{1a}$ in General Formula (Ia) is a substituent represented by General Formula (IIa)

[Chem. 12]

(IIa)

wherein p represents an integer of from 1 to 5, preferably an integer of from 2 to 4, or by General Formula (IIIa)

[Chem. 13]

(IIIa)

wherein p is as defined above.

In particular, between General Formulae (IIa) and (IIIa), the $R^{1a}$ is preferably a substituent represented by General Formula (IIa).

Examples of silsesquioxanes whose generation number n is 2 include a silsesquioxane (hereinafter sometimes referred to as "silsesquioxane b") wherein the $R^{1a}$ is a substituent represented by General Formula (IIb)

[Chem. 14]

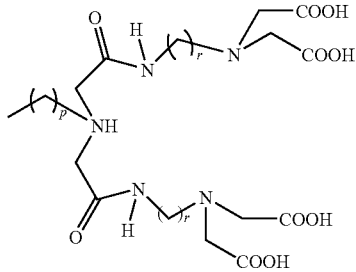
(IIb)

wherein p is as defined above; and each r is the same or different, and represents an integer of from 2 to 10, preferably an integer of from 2 to 4.

Examples of silsesquioxanes whose generation number n is 3 include a silsesquioxane (hereinafter sometimes referred to as "silsesquioxane c") wherein the $R^{1a}$ is a substituent represented by General Formula (IIc)

[Chem. 15]

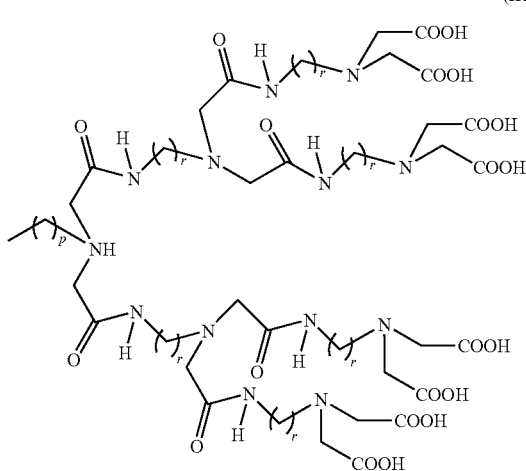
(IIc)

wherein p and r are as defined above.

The contrast agent of the present invention contains, as the essential component, a silsesquioxane complex formed by the coordination of a silsesquioxane represented by General Formula (I), preferably the silsesquioxanes A to C, more preferably the silsesquioxanes a to c, to a metal ion, preferably a paramagnetic metal ion, more preferably $Gd^{3+}$.

In particular, the contrast agent of the present invention can be suitably used as a contrast agent for MRI, more preferably as a positive contrast agent.

Process for Producing Silsesquioxane

The process for producing a silsesquioxane of the present invention is a process for producing a silsesquioxane represented by General Formula (I2)

[Chem. 16]

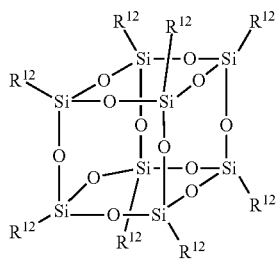
(I2)

wherein $R^{12}$, the same or different, is a substituent bonded to Si through a carbon atom, the substituent having, at its terminal, a group represented by General Formula (II2)

[Chem. 17]

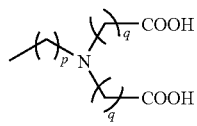
(II2)

wherein p represents an integer of from 1 to 5, preferably an integer of from 2 to 4; and each q is the same or different, and represents an integer of from 1 to 5, preferably an integer of 1 or 2, or a group represented by General Formula (III2)

[Chem. 18]

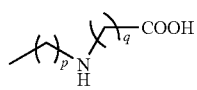
(III2)

wherein p and q are as defined above, the process comprising (1) reacting an amino compound or a salt thereof represented by General Formula (IV)

[Chem. 19]

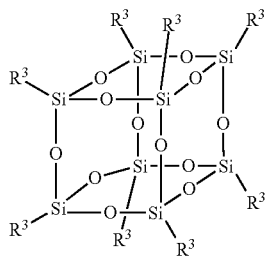
(IV)

wherein each $R^3$, the same or different, is a substituent bonded to Si through a carbon atom, the substituent having —$NH_2$ at its terminal, with an ester compound represented by General Formula (V)

[Chem. 20]

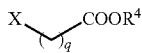
(V)

wherein $R^4$ represents alkyl group, aralkyl group, or acyl group; X represents Cl, Br, or I; and q is as defined above, thereby obtaining a silsesquioxane (I1) represented by General Formula (I1)

[Chem. 21]

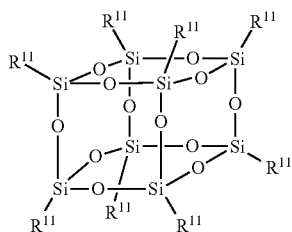
(I1)

wherein each $R^{11}$ is the same or different, and represents a substituent having

[Chem. 22]

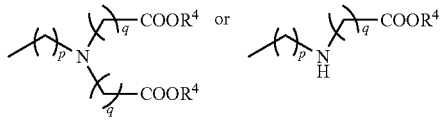

at its terminal, and (2) converting $R^4$ of silsesquioxane (I1) obtained in Step (1) to a hydrogen atom.

The silsesquioxane in General Formula (I), whose generation number n is 1 or higher, can be suitably produced by reacting the amino compound or a salt thereof in General Formula (IV) with the ester compound in General Formula (V), and converting $R^4$ of the silsesquioxane (I1) to a hydrogen atom.

(Step (1))

In Step (1), the amino compound or a salt thereof is reacted with the ester compound to obtain the silsesquioxane (I1).

The amino compound is a silsesquioxane wherein the $R^3$ is a substituent having a —$NH_2$ group at its terminal. Examples of the amino compound include a silsesquioxane wherein the $R^3$ is a substituent having —$NH_3Cl$ or the like.

Preferably, each $R^3$ in General Formula (IV) is the same in view of easy production of the silsesquioxane in General Formula (I2), which corresponds to General Formula (IV). In this case, each $R^{12}$ in General Formula (I2) corresponding to General Formula (IV) is usually the same.

The $R^4$ is the same as the $R^2$. In particular, the $R^4$ is preferably an alkyl group, more preferably a $C_{1-5}$ alkyl group, and further preferably a tert-butyl group.

(Step (2))

In Step (2), $R^4$ of the silsesquioxane (I1) obtained in Step (1) is converted to a hydrogen atom to obtain the silsesquioxane (I2).

The method of converting $R^4$ of the silsesquioxane (I1) to a hydrogen atom is not particularly limited insofar as the method can convert an ester moiety to a carboxylic acid group. For example, hydrolysis, dealkylation using formic acid and the like (deprotection process), and other like methods can be used.

According to the process for producing a silsesquioxane of the present invention, a silsesquioxane whose generation number n is 1 or higher, for example, can be easily produced.

Below, the process for producing a silsesquioxane of the present invention is described in detail, taking the production of silsesquioxanes A, B, and C as representative examples. Note that, in the description, silsesquioxane A is referred to as silsesquioxane (IA2), silsesquioxane B as silsesquioxane (IB2), and silsesquioxane C as silsesquioxane (IC2).

<Production Process of Silsesquioxane A>

The production process of silsesquioxane (IA2) represented by General Formula (IA2)

[Chem. 23]

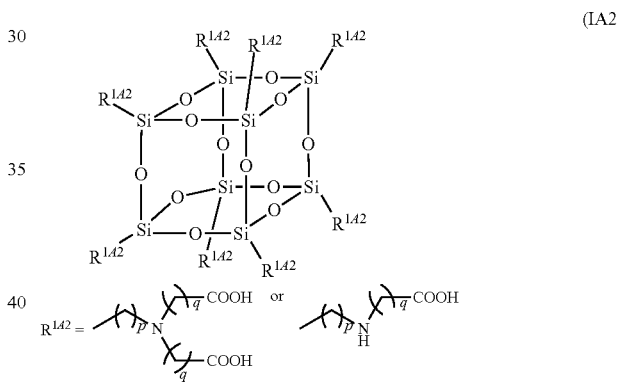
(IA2)

wherein p and q are as defined above; and each $R^{1A2}$ the same or different, comprises (1) reacting an amino compound or a salt thereof represented by General Formula (IVA)

[Chem. 24]

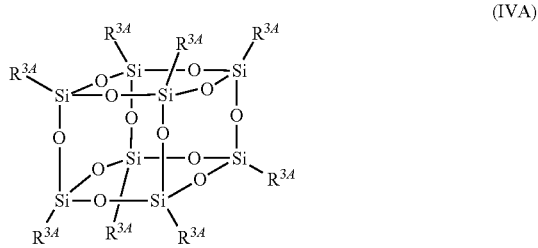
(IVA)

wherein each $R^{3A}$ is the same or different, and represents —$(CH_2)_p$—$NH_2$ (p is as defined above), with an ester compound represented by General Formula (VA)

[Chem. 25]

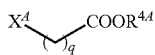
(VA)

wherein $R^{4A}$ represents alkyl group, aralkyl group, or acyl group; $X^A$ represents Cl, Br, or I; and q is as defined above, thereby obtaining silsesquioxane (IA1) represented by General Formula (IA1)

[Chem. 26]

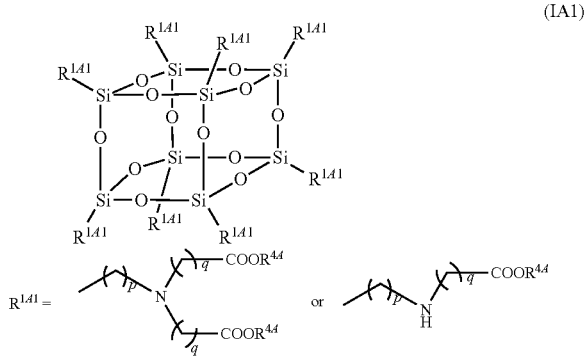
(IA1)

wherein p, q, and $R^{4A}$ are as defined above; and each $R^{1A1}$ is the same or different, and (2) converting $R^{4A}$ of silsesquioxane (IA1) obtained in Step (1) to a hydrogen atom.

(Step (1))

In Step (1), the amino compound or a salt thereof is reacted with the ester compound to obtain the silsesquioxane (IA1).

In the $R^{3A}$, p is preferably an integer of from 2 to 4.

The amino compound preferably forms a salt, and more preferably has an —$NH_3Cl$ group at the terminal of each $R^{3A}$.

The amino compound or a salt thereof can be easily produced by conventional methods. For example, the amino compound can be produced by reacting 3-aminopropyltriethoxysilane in methanol, in the presence of hydrochloric acid. The amino compound is also commercially available.

The $R^{4A}$ is preferably an alkyl group, more preferably a $C_{1-5}$ alkyl group, and further preferably a tert-butyl group.

Preferably, the $X^A$ is Br.

Preferably, the q is an integer of 1 or 2.

The silsesquioxane (IA1) can be produced by, for example, reacting the above-described amino compound or a salt thereof with the above-described ester compound in an organic solvent, in the presence of a base.

A tertiary amine, potassium carbonate, or the like may be used as the base. These bases may be used alone, or in a combination of two or more. In particular, the base is preferably a tertiary amine, more preferably N,N-diisopropylethylamine (DIPEA). The use amount of the base is usually about 100 to about 500 equivalents, preferably about 100 to about 200 equivalents, with respect to the amino compound or a salt thereof.

For example, N,N-dimethylformamide (DMF), acetonitrile, alcohol, acetone, or the like may be used as the organic solvent. These organic solvents may be used alone, or in a combination of two or more. The organic solvent is particularly preferably DMF.

When obtaining silsesquioxane (IA1) wherein the $R^{1A1}$ is

[Chem. 27]

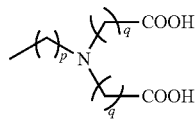

the used ratio of the amino compound or a salt thereof to the ester compound is usually 1 mol:about 100 to about 500 mol, preferably 1 mol:about 100 to about 200 mol.

Further, when obtaining silsesquioxane (IA1) wherein the $R^{1A1}$ is

[Chem. 28]

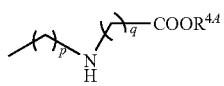

the amino compound or a salt thereof and the ester compound are usually used in a ratio of 1 mol:about 8 to about 10 mol, preferably in a ratio of 1 mol:about 8 to about 9 mol.

The reaction temperature in the reaction is usually 60° C. to 80° C., preferably 60° C. to 70° C.

The reaction time in the reaction can be suitably set according to the reaction temperature and the like. Usually, it is set for 16 to 24 hours, preferably 16 to 18 hours.

The reaction pressure in the reaction is not particularly limited. A normal pressure is sufficient.

Preferably, the reaction is carried out in an inert gas atmosphere, such as argon gas, nitrogen gas, or the like.

After the reaction, according to the need, the resulting silsesquioxane (IA1) can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

(Step (2))

$R^{4A}$ of silsesquioxane (IA1) obtained in Step (1) is converted to a hydrogen atom to obtain the silsesquioxane (IA2).

According to the above step, a silsesquioxane having a substituent with a carboxylic acid group at its terminal can be obtained. The method of converting $R^{4A}$ to a hydrogen atom is the same as the method of converting the $R^4$ to a hydrogen atom.

For example, when $R^{4A}$ of silsesquioxane (IA1) is a tert-butyl group, the tert-butyl group is suitably removed using formic acid, and a carboxylic acid group can thereby be obtained. In this case, the use amount of formic acid is not particularly limited. It is usually 500 to 2,000 equivalents, preferably 1,000 to 1,500 equivalents, with respect to the silsesquioxane (IA1). Further, the reaction is preferably carried out under heated reflux. A reaction time of 16 to 24 hours is sufficient.

After the reaction, according to the need, the resulting silsesquioxane (IA2) can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

Silsesquioxane (IA2) can be suitably produced by the process described above.

<Production Process of Silsesquioxane B>

A production process of silsesquioxane (IB2) represented by General Formula (IB2)

[Chem. 29]

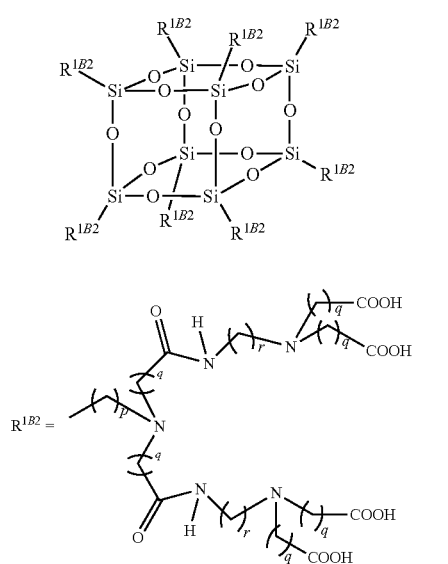

(IB2)

wherein p and q are as defined above; each r is the same or different, and represents an integer of from 2 to 10; and each $R^{1B2}$ is the same or different, comprises (1) reacting the amino compound or a salt thereof with an ester compound represented by General Formula (VB1)

[Chem. 30]

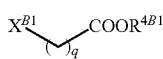

(VB1)

wherein $R^{4B1}$ represents alkyl group, aralkyl group, or acyl group; $X^{B1}$ represents Cl, Br, or I; and q is as defined above, to obtain silsesquioxane (IB1) represented by General Formula (IB1)

[Chem. 31]

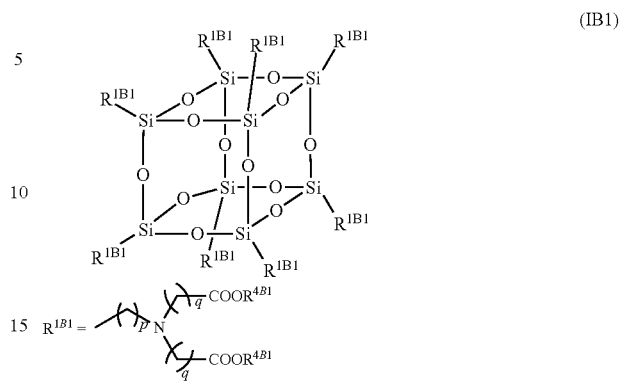

(IB1)

wherein p, q, and $R^{4B1}$ are as defined the above, (2) reacting silsesquioxane (IB1) obtained in Step (1) with a diamine compound represented by General Formula (VIB)

[Chem. 32]

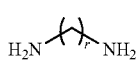

(VIB)

wherein r is as defined above,
thereby obtaining an amide compound represented by General Formula (IVB)

[Chem. 33]

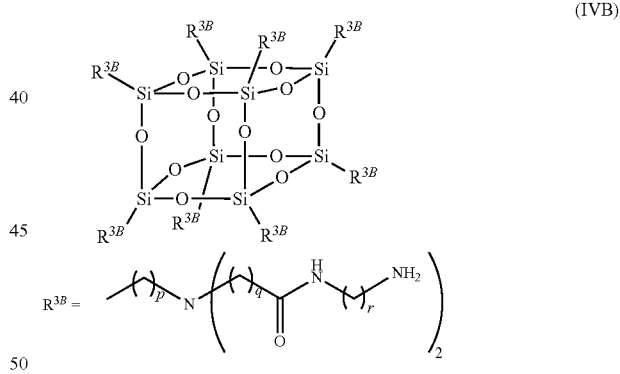

(IVB)

wherein p, q, and r are as described above; and each $R^{3B}$ is the same or different, (3) reacting the amide compound obtained in Step (2) with an ester compound represented by General Formula (VB2)

[Chem. 34]

(VB2)

wherein $R^{4B2}$ represents alkyl group, aralkyl group, or acyl group; $X^{B2}$ represents Cl, Br, or I; and q is as defined above, to obtain silsesquioxane (IB1') represented by General Formula (IB1')

[Chem. 35]

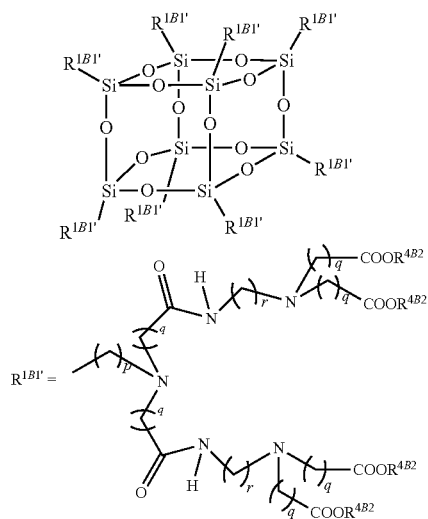

(IB1')

wherein p, q, and r are as defined above; and each $R^{1B1'}$ is the same or different, and (4) converting $R^{4B2}$ of silsesquioxane (IB1') obtained in Step (3) to a hydrogen atom.

(Step (1))

In Step (1), the amino compound or a salt thereof is reacted with the ester compound to obtain the silsesquioxane (IB1).

In the $R^{3A}$, p is preferably an integer of from 2 to 4.

The amino compound preferably forms a salt, and more preferably has an —$NH_3Cl$ group at the terminal of each $R^{3A}$.

The $R^{4B1}$ is preferably an alkyl group, more preferably a $C_{1-5}$ alkyl group, and further preferably an ethyl group.

Preferably, the $X^{B1}$ is Br.

Preferably, q is an integer of from 1 to 5, with an integer of 1 or 2 being more preferred.

The silsesquioxane (IB1) can be produced by, for example, reacting the amino compound or a salt thereof with the ester compound in an organic solvent in the presence of a base.

The bases as described above may be used. The use of DIPEA is particularly preferred. The use amount of the base is usually about 100 to about 500 equivalents, preferably about 100 to about 200 equivalents, with respect to the amino compound or a salt thereof.

The organic solvent is as described above. DMF is particularly preferred.

The used ratio of the amino compound or a salt thereof to the ester compound is usually 1 mol:about 100 to about 500 mol, preferably 1 mol:about 100 to about 200 mol.

The reaction temperature in the reaction is usually 60° C. to 80° C., preferably 60° C. to 70° C.

The reaction time in the reaction can be suitably set according to the reaction temperature and the like. Usually, it is set for 16 to 24 hours, preferably 16 to 18 hours.

The reaction pressure in the reaction is not particularly limited. A normal pressure is sufficient.

Preferably, the reaction is carried out in an inert gas atmosphere, such as argon gas, nitrogen gas, or the like.

After the reaction, according to the need, the resulting silsesquioxane (IB1) can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

(Step (2))

In Step (2), silsesquioxane (IB1) obtained in Step (1) is reacted with the diamine compound to obtain the amide compound.

Preferably, the r is an integer of from 2 to 4.

The used ratio of the silsesquioxane (IB1) to the diamine compound is usually 1 mol:about 4,000 to about 10,000 mol, preferably 1 mol:about 4,000 to about 6,000 mol.

The reaction temperature in the reaction is usually 60° C. to 80° C., preferably 60° C. to 70° C.

The reaction time in the reaction can be suitably set according to the reaction temperature and the like. Usually, it is set for 16 to 24 hours, preferably 16 to 18 hours.

The reaction pressure in the reaction is not particularly limited. A normal pressure is sufficient.

Preferably, the reaction is carried out in an inert gas atmosphere, such as argon gas, nitrogen gas, or the like.

After the reaction, according to the need, the resulting amide compound can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

(Step (3))

In Step (3), the amide compound obtained in Step (2) is reacted with the ester compound to obtain the silsesquioxane (IB1').

The $R^{4B2}$ is preferably an alkyl group, more preferably a $C_{1-5}$ alkyl group, and further preferably a tert-butyl group.

Preferably, the $X^{B2}$ is Br.

Preferably, q is an integer of 1 or 2.

The silsesquioxane (IB1') can be produced by, for example, reacting the amino compound or a salt thereof with the ester compound in an organic solvent, in the presence of a base.

The bases as described above may be used. DIPEA is particularly preferred. The use amount of the base is usually about 200 to about 500 equivalents, preferably about 200 to about 300 equivalents, with respect to the amino compound or a salt thereof.

The organic solvents as described above may be used. DIPEA is particularly preferred.

The used ratio of the amide compound to the ester compound is usually 1 mol:about 200 to about 500 mol, preferably 1 mol:about 200 to about 300 mol.

The reaction temperature in the reaction is usually 60° C. to 80° C., preferably 60° C. to 70° C.

The reaction time in the reaction can be suitably set according to the reaction temperature and the like. Usually, it is set for 16 to 24 hours, preferably 16 to 18 hours.

The reaction pressure in the reaction is not particularly limited. A normal pressure is sufficient.

Preferably, the reaction is carried out in an inert gas atmosphere, such as argon gas, nitrogen gas, or the like.

After the reaction, according to the need, the resulting silsesquioxane (IB1') can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

(Step (4))

In Step (4), $R^{4B2}$ of the silsesquioxane (IB1') obtained in Step (3) is converted to a hydrogen atom to obtain the silsesquioxane (IB2).

The method of converting $R^{4B2}$ to a hydrogen atom is the same as the method of converting the $R^4$ to a hydrogen atom.

For example, when $R^{4B2}$ of silsesquioxane (IB1') is a tert-butyl group, the tert-butyl group is suitably removed using formic acid, and a carboxylic acid group can thereby be obtained. In this case, the use amount of formic acid is not particularly limited: it is usually 5,000 to 15,000 equivalents, preferably 5,000 to 10,000 equivalents, with respect to the silsesquioxane (IB1'). Further, the reaction is preferably carried out under heated reflux. A reaction time of 16 to 24 hours is sufficient.

After the reaction, according to the need, the resulting silsesquioxane (IB2) can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

Silsesquioxane (IB2) can be suitably produced by the process described above.

<Production Process of Silsesquioxane C>

The production process of silsesquioxane (IC2) represented by General Formula (IC2)

[Chem. 36]

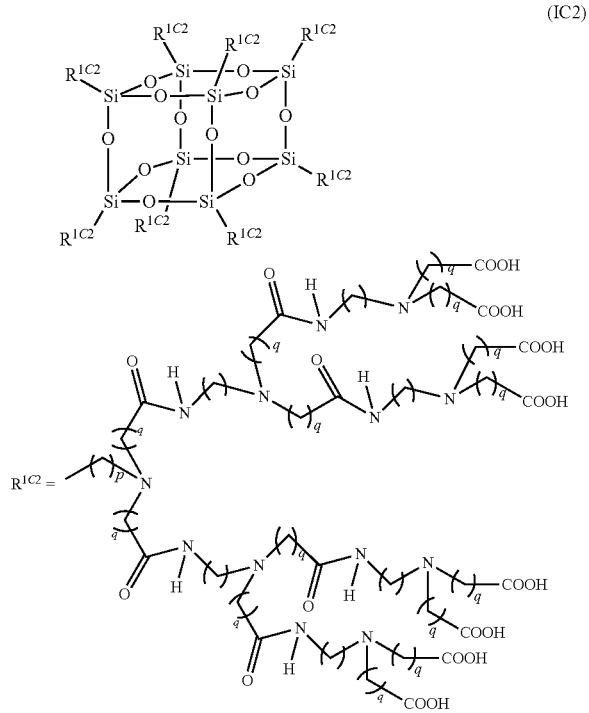

(IC2)

wherein p, q, and r are as defined above; and each $R^{1C2}$ is the same or different, comprises (1) reacting the silsesquioxane (IB1') with a diamine compound represented by General Formula (VIC)

[Chem. 37]

(VIC)

wherein r is as defined above, thereby obtaining an amide compound represented by General Formula (IVC)

[Chem. 38]

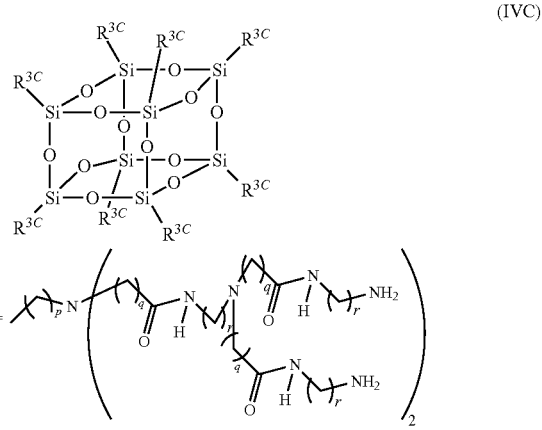

(IVC)

wherein p, q, and r are as defined above; and each $R^{3C}$ the same or different, (2) reacting the amide compound obtained in Step (1) with an ester compound represented by General Formula (VC)

[Chem. 39]

(VC)

wherein $X^C$ represents Cl, Br, or I; $R^{4C}$ represents alkyl group, aralkyl group, or acyl group; and q is as defined above, thereby obtaining silsesquioxane (IC1) represented by General Formula (IC1)

[Chem. 40]

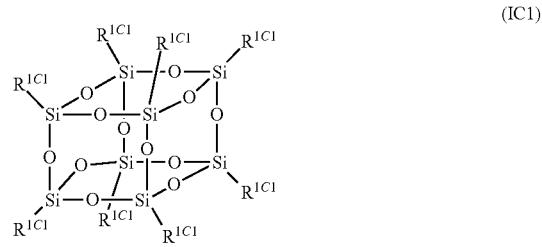

(IC1)

-continued

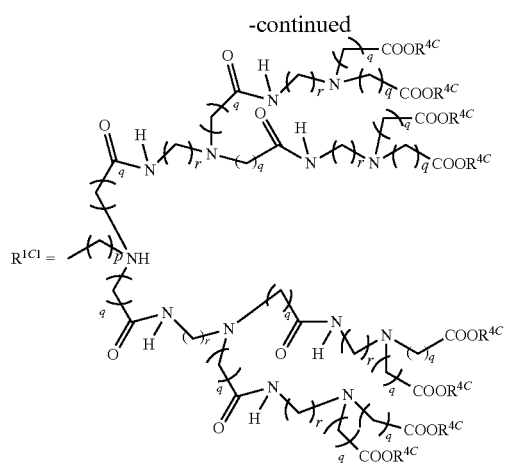

wherein p, q, r, and $R^{4C}$ are as defined above; and each $R^{1C1}$ is the same or different, and (3) converting $R^{4C}$ of silsesquioxane (IC1) obtained in Step (2) to a hydrogen atom.

(Step (1))

In Step (1), the silsesquioxane (IB1') is reacted with the diamine compound to obtain the amide compound.

The silsesquioxane (IB1'), which is an intermediate in the production of silsesquioxane B, may be suitably used as a silsesquioxane (IB1').

Preferably, the p is an integer of from 2 to 4.

Preferably, the q is an integer of 1 or 2.

Preferably, the r is an integer of from 2 to 4.

$R^{4B2}$ of silsesquioxane (IB1') used in Step (1) is preferably a $C_{1-5}$ alkyl group, more preferably an ethyl group.

The used ratio of the silsesquioxane (IB1') to the diamine compound is usually 1 mol:about 10,000 to about 50,000 mol, preferably 1 mol:about 20,000 to about 30,000 mol.

The reaction temperature in the reaction is usually 60° C. to 80° C., preferably 60° C. to 70° C.

The reaction time in the reaction can be suitably set according to the reaction temperature and the like. Usually, it is set for 16 to 24 hours, preferably 16 to 18 hours.

The reaction pressure in the reaction is not particularly limited. A normal pressure is sufficient.

Preferably, the reaction is carried out in an inert gas atmosphere, such as argon gas, nitrogen gas, or the like.

After the reaction, according to the need, the resulting amide compound can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

(Step (2))

In Step (2), the amide compound obtained in Step (1) is reacted with the ester compound to obtain the silsesquioxane (IC1).

The $R^{4C}$ is preferably an alkyl group, more preferably a $C_{1-5}$ alkyl group, and further preferably a tert-butyl group.

Preferably, the $X^C$ is Br.

Preferably, q is an integer of from 1 to 3, with an integer of 1 or 2 being more preferred.

The silsesquioxane (IC1) can be produced by, for example, reacting the amino compound or a salt thereof with the ester compound in an organic solvent in the presence of a base.

The base is as described above. The use of DIPEA is particularly preferred. The use amount of the base is usually about 500 to about 2,000 equivalents, preferably about 1,000 to about 1,500 equivalents, with respect to the amino compound or a salt thereof.

The organic solvent is as described above.

DMF is particularly preferred.

The used ratio of amide compound to the ester compound is usually 1 mol:about 80 to about 160 mol, preferably 1 mol:about 80 to about 100 mol.

The reaction temperature in the reaction is usually 60° C. to 80° C., preferably 60° C. to 70° C.

The reaction time in the reaction can be suitably set according to the reaction temperature and the like. Usually, it is set for 16 to 24 hours, preferably 16 to 18 hours.

The reaction pressure in the reaction is not particularly limited. A normal pressure is sufficient.

Preferably, the reaction is carried out in an inert gas atmosphere, such as argon gas, nitrogen gas, or the like.

After the reaction, according to the need, the resulting silsesquioxane (IC1) can be easily isolated from the reaction mixture by conventional isolation procedures, and further purified by conventional purification means. Examples of conventional isolation procedures include a method in which a reaction solution obtained after the reaction is vacuum-dried, an organic solvent extraction method, a chromatography method, a recrystallization method, a distillation method, etc.

(Step (3))

$R^{4C}$ of silsesquioxane (IC1) obtained in Step (2) is converted to a hydrogen atom to obtain the silsesquioxane (IC2).

The method of converting $R^{4C}$ to a hydrogen atom is the same as the method of converting the $R^4$ to a hydrogen atom.

For example, when $R^{4C}$ of silsesquioxane (IC1) is a tert-butyl group, the tert-butyl group is suitably removed using formic acid, and a carboxylic acid group can thereby be obtained. In this case, the use amount of formic acid is not particularly limited; however, it is usually 10,000 to 50,000 equivalents, preferably 20,000 to 30,000 equivalents, with respect to the silsesquioxane (IC1). Further, the reaction is preferably carried out under heated reflux. A reaction time of 16 to 24 hours is sufficient.

After the reaction, according to the need, the resulting silsesquioxane (IC2) can be easily isolated from the reaction mixture by conventional isolation procedures, and further purified by conventional purification means. Examples of conventional isolation procedures include an organic solvent extraction method, a chromatography method, a recrystallization method, a distillation method, etc.

Silsesquioxane (IC2) can be suitably produced by the process described above.

Production Process of Contrast Agent

The contrast agent of the present invention can be produced by conventional methods, except that the silsesquioxane is used as a chelating ligand for a metal ion. For example, the contrast agent can be produced by adding a metal ion to an aqueous solution of the silsesquioxane.

The concentration of the silsesquioxane in the aqueous solution is usually 100 to 1,000 µM, preferably 100 to 500 µM.

Further, the amount of the metal ion to be added is not particularly limited. When $Gd^{3+}$ is used as the metal ion, the amount of $Gd^{3+}$ to be added is usually 100 to 1,000 µM, preferably 100 to 500 µM.

The contrast agent of the present invention may be used as a contrast agent for MRI (magnetic resonance imaging), X-ray CT (computed tomography), ultrasound imaging, and scintigraphy. It is particularly suitably used as a contrast agent for MRI.

The contrast agent can be administered either parenterally or orally.

When the contrast agent is parenterally administered, the contrast agent may further contain known additives such as solvents, suspending agents, etc., used for the production of injection products. Examples of the additives include water, propylene glycol, polyethylene glycol, benzyl alcohol, ethyl oleate, lecithin, etc. These additives may be used alone, or in a combination of two or more.

Further, when the contrast agent is orally administered, the contrast agent is administered alone or with a pharmaceutically acceptable carrier. Specifically, the contrast agent is orally administered in the forms of, for example, granules, fine granules, powders, tablets, hard syrup, soft capsules, syrups, emulsions, suspensions, liposomes, solutions, etc. An excipient may be used when forming the granules, fine granules, powders, and tablets. Examples of the excipient include lactose, sucrose, starch, talc, cellulose, dextrin, kaolin, calcium carbonate, etc. These excipients may be used alone, or in a combination of two or more. A generally used inactive diluent may be used when forming the emulsions, syrups, suspensions, and solutions. Examples of the diluent include vegetable oil and the like. The contrast agent may further contain known additives. Examples of the additives include humectants, suspension auxiliary agents, sweeteners, fragrances, colorants, preservatives, etc. These additives may be used alone, or in a combination of two or more. Further, the contrast agent formed in the emulsion or the like may be placed in a capsule made of an absorbable substance, like gelatin.

The dosage of administration of the contrast agent of the present invention is not particularly limited: it is 0.1 mg to 10 g, preferably 1 mg to 5 g, per adult in one diagnosis.

Effects of the Invention

The contrast agent of the present invention is particularly advantageous in the following points (1) to (4).
(1) The contrast agent of the present invention has contrast performance that is approximately 10 times higher than that of commercially available contrast agents. This is likely because the molecular rotation is suppressed due to the rigidity of the basic skeleton comprising the above-described silsesquioxane.
(2) The contrast agent of the present invention allows high-sensitivity detection of target cells such as tumors and the like, even though the concentration of the contrast agent is low. Specifically, the contrast agent of the present invention can produce excellent contrast in MRI images, particularly in T1 weighted images.
(3) The toxicity of the contrast agent of the present invention is low because the concentration of the contrast agent is low, and the release of free metal ions (particularly $Gd^{3+}$) does not easily occur. Accordingly, the risk of adverse effects is very low.
(4) The contrast agent of the present invention can be produced more easily and at lower cost than conventional contrast agents.

DESCRIPTION OF EMBODIMENTS

The present invention is more specifically explained with reference to Examples and Comparative Examples. However, the present invention is not limited to these Examples.

EXAMPLE 1

Production of Silsesquioxane A

Preparation of Amino Compound Salt 800 mL of methanol and 135 mL of a concentrated hydrochloric acid were mixed in a 1 L recovery flask, and 100 mL (0.427 mol) of 3-aminopropyltriethoxysilane was added thereto. The mixture was stirred at room temperature (25° C.) for 48 hours until a white precipitate was produced. After filtering the precipitate, the obtained residue was washed with methanol to give an amino compound salt (18.8 g, yield=30%) represented by General Formula (IVA) wherein each $R^{3,4}$ represents —$(CH_2)_3$—$NH_3Cl$.

Step (1)

Thereafter, 1 g (0.852 mmol) of the obtained amino compound salt, 15 mL (0.102 mol, 120 equivalents with respect to the amino compound salt) of DIPEA, 15 mL (0.102 mol, 120 equivalents with respect to the amino compound salt) of tert-butyl bromoacetate and 100 mL of DMF were placed in a 500 mL recovery flask, and the mixture was reacted at 60° C. for 16 hours in a nitrogen atmosphere. The resulting reaction liquid was dried under vacuum to give a yellow solid.

Step (2)

100 mL (2.65 mol) of a formic acid was placed in the recovery flask containing the yellow solid obtained in Step (1). The flask was heated under reflux for 24 hours to give a reaction liquid (deprotection step). After removing the formic acid from the obtained reaction liquid using an evaporator, 200 mL of methanol was added to cause precipitation. After filtering the precipitate, the obtained residue was washed with methanol to give silsesquioxane A (240 mg, yield=16%) represented by General Formula (IA2) wherein each $R^{1,42}$ represents the following Chemical Formula.

[Chem. 41]

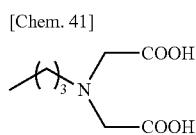

The $^1$H NMR spectrum of the obtained silsesquioxane A is as follows.

$^1$H NMR (D$_2$O, 400 MHz) δ 3.92 (s, 32H), 3.33 (brs, 16H), 1.83 (brs, 16H), 0.80 (brs, 16H): $^{13}$C NMR (D$_2$O, 100 MHz) δ161.3, 50.4, 48.2, 26.4, 9.9: $^{29}$Si NMR (D$_2$O, 80 MHz) δ−67.2: MALDI-TOF [(M+H)$^+$] calcd. 1811.08, found 1812.01.

EXAMPLE 2

Production of Silsesquioxane B

Step (1)

1 g (0.853 mmol) of the amino compound salt obtained in Example 1, 15 ml of DIPEA (86.1 mmol, 100 equivalents with respect to the amino compound salt), 9.5 mL (86.1 mmol, 100 equivalents with respect to the amino compound salt) of ethylbromoacetate and 50 mL of DMF were placed in a 500 mL recovery flask. The mixture was reacted at 60° C. for 16 hours in a nitrogen atmosphere to give a reaction liquid. After removing DMF from the reaction liquid using an evaporator, 200 mL of ethyl acetate was added to give a mixed solution. The mixed solution was washed three times with 200 mL of water, and then washed once with 200 mL of a saturated sodium chloride aqueous solution. The organic layer obtained by the washing was concentrated to give a silsesquioxane (IB1) (1.07 g, 0.529 mmol, yield=62%) represented by General Formula (IB1) wherein p represents 3, q represents 1, and $R^{4B}$ represents —$CH_2CH_3$.

Step (2)

Thereafter, 200 mL (2.24 mol) of ethylenediamine was added, and the silsesquioxane (IB1) and the ethylenediamine were reacted at 60° C. for 16 hours in a nitrogen atmosphere to give a reaction liquid. The reaction liquid was dried using a vacuum pump to give an amide compound (1.3 g, 0.523 mmol, yield=99%) represented by above General Formula (IVB) wherein p represents 3, q represents 1, and r represents 2.

Step (3)

1 g (0.403 mmol) of the amide compound obtained in Step (2), 15 ml of DIPEA (0.102 mol, 250 equivalents with respect to the amide compound), 15 mL (0.102 mol, 250 equivalents with respect to the amide compound) of tert-butyl bromoacetate and 100 mL of DMF were placed in a 500 mL recovery flask. The mixture was reacted at 60° C. for 16 hours under a nitrogen atmosphere to give a reaction liquid. The reaction liquid was dried under vacuum to give a silsesquioxane (IB1') represented by above General Formula (IB1') wherein p represents 3, q represents 1, r represents 2, and $R^{4B2}$ represents tert-butyl group.

Step (4)

100 mL (2.65 mol) of a formic acid was placed in the recovery flask containing a yellow solid obtained in Step (3). The flask was heated under reflux for 24 hours to give a reaction liquid (deprotection step). After removing the formic acid from the obtained reaction liquid using an evaporator, 200 mL of methanol was added to cause precipitation. After filtering the precipitate, the obtained residue was washed with methanol to give silsesquioxane B (1.05 mg, yield=60%) represented by General Formula (IB2) wherein p represents 3, q represents 1, and r represents 2.

$^1$H NMR ($D_2O$, 400 MHz) δ 3.72 (br, 96H), 3.56 (brs, 32H), 3.30 (brs, 32H), 3.20 (brs, 16H), 1.71 (brs, 16H), 0.67 (brs, 16H): $^{13}$C NMR ($D_2O$, 100 MHz) δ175.1, 172.1, 61.7, 61.2, 59.2, 51.5, 37.5, 20.8, 10.2: $^{29}$Si NMR ($D_2O$, 80 MHz) δ–67.4: ESI-TOF [(M+3H)$^{3+}$] calcd. 1454.8, found 1454.8.

EXAMPLE 3

Production of Silsesquioxane C

Production of Silsesquioxane IB1'

1.0 g (0.403 mmol) of the amide compound obtained in Step (2) of Example 2, 15 ml of DIPEA (86.1 mmol, 215 equivalents with respect to the amide compound), 9.5 mL (86.1 mmol, 215 equivalents with respect to the amide compound) of ethylbromoacetate and 50 mL of DMF were placed in a 500 mL recovery flask. The mixture was reacted at 60° C. for 16 hours in a nitrogen atmosphere to give a reaction liquid. After concentrating the obtained reaction liquid, 200 mL of ethyl acetate was added thereto to give a mixed solution. The mixed solution was washed three times with 200 mL of water, and then washed once with 200 mL of a saturated sodium chloride aqueous solution. The organic layer obtained by the washing was concentrated to give silsesquioxane (IB1') (yellow solid, 548 mg, 0.104 mmol, yield-26%) represented by above General Formula (IB1') wherein p represents 3, q represents 1, r represents 2 and $R^{4B2}$ represents ethyl group.

Step (1)

Then, 200 mL (2.24 mol) of ethylenediamine was added, and the silsesquioxane (IB1') and the ethylenediamine were reacted at 60° C. for 16 hours under a nitrogen atmosphere to give a reaction liquid. The reaction liquid was dried under vacuum to give an amide compound (589 mg, 0.103 mmol, yield=99%) represented by above General Formula (IVC) wherein p represents 3, q represents 1, and r represents 2.

Step (2)

15 ml of DIPEA (0.102 mol, 1,000 equivalents with respect to the amide compound), 15 mL (0.102 mol, 1,000 equivalents with respect to the amide compound) of tert-butyl bromoacetate and 100 mL of DMF were placed in a recovery flask containing the amide compound obtained in Step (1). The mixture was reacted at 60° C. for 16 hours in a nitrogen atmosphere to give a reaction liquid. The reaction liquid was dried under vacuum to give silsesquioxane (IC1) (yellow solid) represented by above General Formula (IC1) wherein p represents 3, q represents 1, r represents 2, and $R^{4C}$ represents tert-butyl group.

Step (3)

100 mL (2.65 mol) of a formic acid was placed in the recovery flask containing the yellow solid obtained in Step (2). The flask was heated under reflux for 24 hours to give a reaction liquid (deprotection step). After removing the formic acid from the obtained reaction liquid using an evaporator, 200 mL of methanol was added to cause precipitation. After filtering the precipitate, the obtained residue was washed with methanol to give silsesquioxane C (169 mg, yield=16%) represented by General Formula (IC2), wherein p represents 3, q represents 1, and r represents 2.

$^1$H NMR ($D_2O$, 400 MHz) δ 3.96 (s, 224H), 3.82 (brs, 96H), 3.35 (brs, 96H), 3.23 (brs, 16H), 1.72 (brs, 16H), 0.65 (brs, 16H): $^{13}$C NMR ($D_2O$, 100 MHz) δ165.5, 164.1, 164.0, 51.9, 51.2, 50.9, 48.7, 46.6, 45.7, 42.7, 36.9, 28.9, 10.7: $^{29}$Si NMR ($D_2O$, 80 MHz) δ–67.3: ESI-TOF [(M+7H)$^{7+}$] calcd. 1342.1, found 1342.2.

EXPERIMENT EXAMPLE 1

Toxicity Evaluation of Contrast Agent

Under a temperature of 298K, changes in heat quantity during titration of 1 mM of $Gd^{3+}$ into the silsesquioxane A aqueous solution (concentration: 100 μM) obtained in Example 1 were measured using an isothermal titration calorimetry (ITC). Through the curve fitting with the obtained spectra, the coordination number of $Gd^{3+}$ and the binding constant of the bond of $Gd^{3+}$ and silsesquioxane A were calculated.

Further, the coordination number and the binding constant during titration using $Mn^{2+}$, $Cu^{2+}$, $Zn^{2+}$ and $Ca^{2+}$ instead of $Gd^{3+}$ were also measured in the same manner.

Table 1 shows the results.

TABLE 1

| Metal Ion | Coordinate Number | Binding Constant |
| --- | --- | --- |
| $Gd^{3+}$ | 2 | $10^{6-7}$ |
| $Mn^{2+}$ | 4 | $10^{3-4}$ |
| $Cu^{2+}$ | 4 | $10^{4-5}$ |
| $Zn^{2+}$ | 4 | $10^4$ |
| $Ca^{2+}$ | 4 or 8 | $\sim 10^3$ |

Table 1 shows that the silsesquioxane A obtained in Example 1 is firmly bonded with $Gd^{3+}$, and that this bond is 1,000 to 10,000 times stronger than that of $Ca^{2+}$, which antagonizes $Gd^{3+}$ in a living body. Accordingly, Table 1 shows that, when using the contrast agent of the present invention, $Gd^{3+}$ does not easily dissociate in a living body, which indicates a high possibility that the contrast agent of the present invention has low toxicity.

EXPERIMENT EXAMPLE 2

Toxicity Evaluation of Contrast Agent

MTT (3-[4,5-dimethylthiazol-2-yl]-2,5-diphenyl tetrazolium bromide) assay was performed using healthy liver cells of a mouse.

The cell culture was performed in a DME culture medium of 37° C. in the presence of 5% carbon dioxide. More specifically, the cells were prepared by a collagenase perfusion method (Seglen P. O., Methods in Cell Biology 1976, 13, 29-83), and the prepared cells were seeded at a 15,000 cells/100 μL/well in 96 well microtiter plates.

One day after the cell incubation, 10 μL of "an aqueous solution of a Gd complex with which a silsesquioxane A is coordinated" or "an aqueous solution of Gd complex with which DOTA (Wako Pure Chemical Ind. Ltd.) is coordinated" was added to each well, and the culture was continued.

These aqueous solutions were prepared by mixing a chelator (silsesquioxane A or DOTA) and gadolinium chloride in water. Their concentrations are adjusted to be ten times greater than the evaluation concentration (concentration of a horizontal axis in FIG. 3) of the Gd complex.

After three more days, 10 μL of MTT (MTT concentration: 5 mg/mL) dissolved in a phosphate buffered saline (PBS) was added to each well, and a four-hour incubation was performed. After removing and washing the supernatant (the culture medium in which the MTT is dissolved), 100 μL each of 10% sodium dodecyl sulfate (SDS) and 0.01 M of ammonium chloride solution was added. After overnight incubation, the cell survival rate was evaluated from the MTT decomposition amount. The MTT decomposition amount was calculated from absorbency at 600 nm of the solution (37° C.) obtained from the overnight incubation. FIG. 3 shows the results.

In FIG. 3, ▲ represents an average cell survival rate (%) when adding a complex of silsesquioxane A and Gd, ■ represents an average cell survival rate (%) when adding a complex of DOTA and Gd, and the vertical bar represents the standard deviation of each cell survival rate.

FIG. 3 shows that the complex of silsesquioxane A and Gd of the present invention containing two Gd atoms has a high cell survival rate compared with a complex of Gd and DOTA containing only one Gd atom. The complex of the present invention has low toxicity.

EXPERIMENT EXAMPLE 3

MRI Image

A contrast agent was prepared using silsesquioxanes A-C obtained in Examples 1 to 3, DOTA (product of Wako Pure Chemical Ind. Ltd.), or DTPA (product of Aldrich), as the ligand of a metal complex. More specifically, each ligand was dissolved in water, and a metal ion was added thereto to prepare an aqueous solution (contrast agent) containing a metal complex.

Table 2 shows, for each aqueous solution, the combination of the ligand and metal ion, the concentration (μM) of the ligand, and the addition amount (μM) of the metal ion.

TABLE 2

| Ligand | Metal Ion | Concentration of ligand in aqueous solution (μM) Concentration of metal ion in aqueous solution (μM) | | | | |
|---|---|---|---|---|---|---|
| Silsesquioxane A | $Gd^{3+}$ | 500 | 250 | 125 | 60 | 30 |
| | | 1,000 | 500 | 250 | 125 | 60 |
| Silsesquioxane B | $Gd^{3+}$ | 500 | 250 | 125 | 60 | 30 |
| | | 2,000 | 1,000 | 500 | 250 | 125 |
| Silsesquioxane C | $Gd^{3+}$ | 500 | 250 | 125 | 60 | 30 |
| | | 4,000 | 2,000 | 1000 | 500 | 250 |
| DOTA | $Gd^{3+}$ | 500 | 250 | 125 | 60 | 30 |
| | | 500 | 250 | 125 | 60 | 30 |
| DTPA | $Gd^{3+}$ | 500 | 250 | 125 | 60 | 30 |
| | | 500 | 250 | 125 | 60 | 30 |
| Silsesquioxane A | $Mn^{2+}$ | 500 | 250 | 125 | 60 | 30 |
| | | 2,000 | 500 | 250 | 125 | 60 |

| Ligand | Metal Ion | Concentration of ligand in aqueous solution (μM) Concentration of metal ion in aqueous solution (μM) | | | | | | |
|---|---|---|---|---|---|---|---|---|
| Silsesquioxane A | $Gd^{3+}$ | 15 | — | — | — | — | — | — |
| | | 30 | | | | | | |
| Silsesquioxane B | $Gd^{3+}$ | 15 | 8 | 4 | 2 | 1 | 0.5 | 0.25 |
| | | 60 | 30 | 15 | 8 | 4 | 2 | 1 |
| Silsesquioxane C | $Gd^{3+}$ | 15 | 8 | 4 | 2 | 1 | 0.5 | 0.25 |
| | | 125 | 60 | 30 | 15 | 8 | 4 | 2 |
| DOTA | $Gd^{3+}$ | 15 | — | — | — | — | — | — |
| | | 15 | | | | | | |
| DTPA | $Gd^{3+}$ | 15 | — | — | — | — | — | — |
| | | 15 | | | | | | |
| Silsesquioxane A | $Mn^{2+}$ | 15 | — | — | — | — | — | — |
| | | 60 | | | | | | |

Each aqueous solution shown in Table 2 was sealed in a glass tube. A T1 weighted image of a proton was taken at 298K, 7T (tesla). The repetition time (TR) was 1,000 ms, and the echo time (TE) was 12 ms. Each glass tube containing one of the aqueous solutions shown in Table 3 was held still in a coil, and an image of the glass tube was taken using a 7T Unity Inova MR scanner (product of Varian Inc.) as a magnetic resonance imager (MRI).

FIG. 4 shows the results.

For comparison, FIG. 4 also shows a T1 weighted image of a glass tube that contains pure water instead of the aqueous solution.

FIG. 4 shows that, for example, in a comparison of two contrast media containing a metal complex having $Gd^{3+}$ as a metal ion, the contrast agent having ligands of silsesquioxane A (Example 1) has a sensitivity ten times greater than the contrast agent having ligands of DOTA or DTPA. Further, the contrast agent having ligands of silsesquioxane B (Example 2) and the contrast agent having ligands of silsesquioxane C (Example 3) have sensitivities 50 to 100 times greater than the contrast agent having ligands of DOTA or DTPA. Accordingly, these contrast media of Examples of the present invention have superior contrast properties.

EXPERIMENT EXAMPLE 4

Contrast Property

The T1 values measured upon the above image-taking using the aqueous solutions in Test Example 3 and the metal ion concentrations for each aqueous solution were applied to the following Formula (1), thereby plotting a graph. A relaxation degree $r_1$ was calculated based on the inclination of the linear curve. The relaxation degree $r_1$ represents the proton relaxation performance per mol of the metal ion ($Gd^{3+}$, $Mn^{2+}$). The relaxation time T1 is an index showing the proton relaxation performance per mol of the contrast agent. The constant "a" represents an inverse of the T1 value of pure water.

$$1/T1 = a + r_1[M] \quad (1)$$

(wherein [M] is a metal ion concentration and "a" is a constant)

For comparison, an aqueous solution was prepared according to the same method as the example using DOTA in Table 2, except that PAMAM (Aldrich) was used as a ligand. With this aqueous solution, the relaxation degree $r_1$ was calculated by the above method.

Table 3 shows the results.

The smaller the T1 value, the greater the contrast performance. Therefore, in the following Table 3, the $Gd^{3+}$-silsesquioxane C complex has the greatest contrast performance.

A greater $r_1$ value indicates a superior contrast performance in a T1 weighted image.

In a comparison of the $Gd^{3+}$-silsesquioxane A complex and the $Gd^{3+}$-silsesquioxane C complex, the $Gd^{3+}$-silsesquioxane A complex has a greater $r_1$ value, and the $Gd^{3+}$-silsesquioxane C complex has a greater T1 value. This is because the number of $Gd^+$ in the complex influences the contrast performance (T1 value). More specifically, the $Gd^{3+}$-silsesquioxane C complex having eight $Gd(s)^{3+}$ coordinate bonds has a greater contrast performance than the $Gd^{3+}$-silsesquioxane A complex having two $Gd(s)^{3+}$ coordinate bonds.

TABLE 3

| Metal Complex | $r_1$ (mM$^{-1}$s$^{-1}$) | T1 (ms) |
|---|---|---|
| $Gd^{3+}$-silsesquioxane A complex | 17.3 | 31 |
| $Gd^{3+}$-silsesquioxane B complex | 12.3 | 20 |
| $Gd^{3+}$-silsesquioxane C complex | 13.6 | 10 |
| $Mn^{2+}$-silsesquioxane A complex | 5.3 | 48 |
| $Gd^{3+}$-PAMAM complex | 7.7 | 66 |
| $Gd^{3+}$-DOTA complex | 4.0 | 269 |
| $Gd^{3+}$-DTPA complex | 3.5 | 311 |
| Water | | 3,500 |

Table 3 shows that the contrast agents containing metal complexes having silsesquioxanes A-C as chelate ligands have significantly high contrast properties, compared with contrast media containing other metal complexes.

Figure 1:
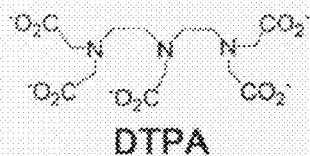
FIG. 1 is a view showing a conventional Gd complex.
Figure 1:
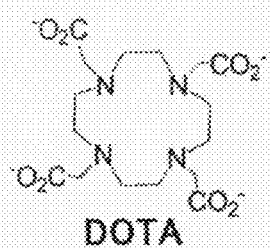
Figure 1:
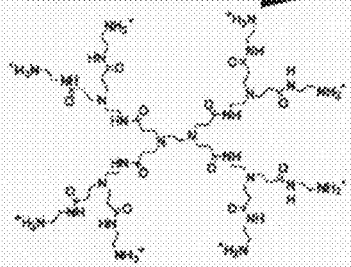
Figure 1:
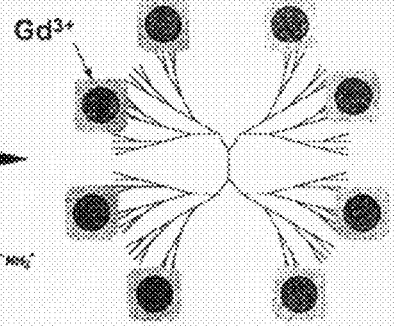
Figure 2:
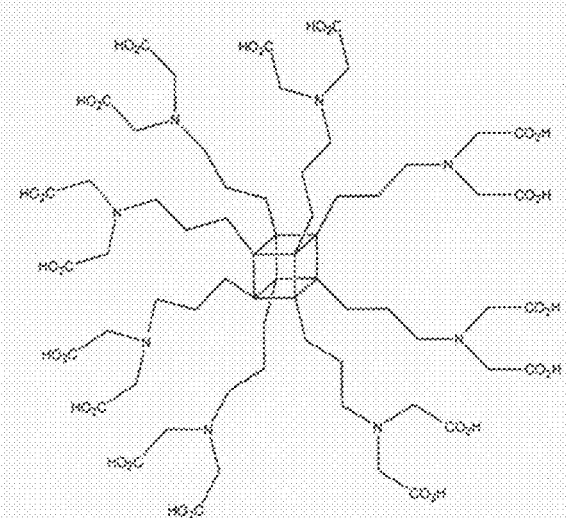
FIG. 2 is a view showing a state of silsesquioxane A coordinated to a metal ion.
Figure 2:
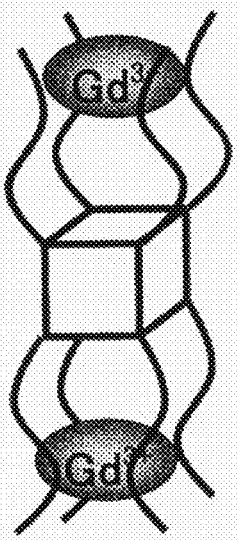
Figure 3:
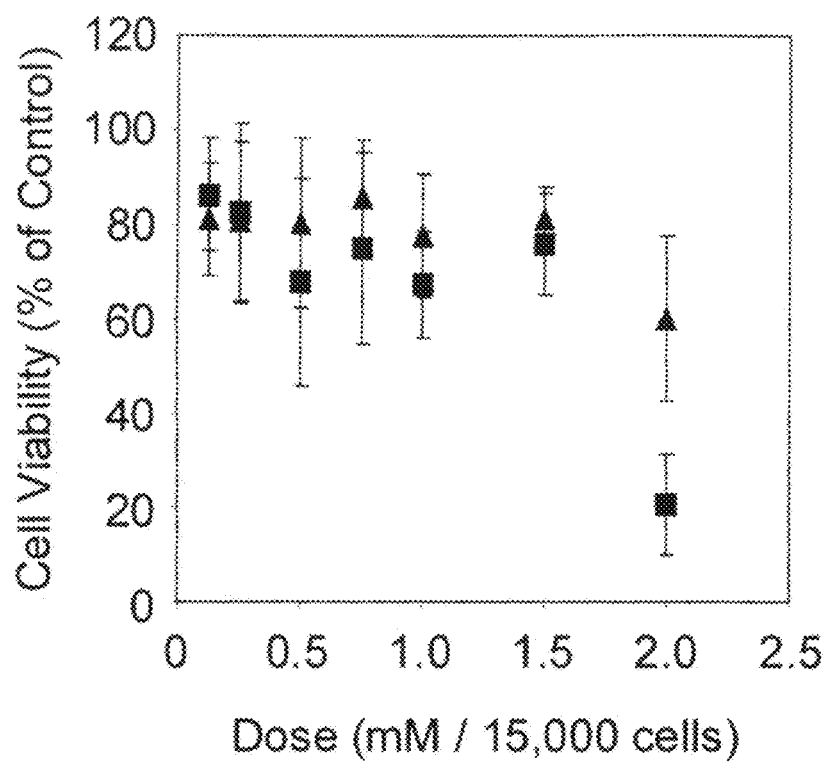
FIG. 3 is a view showing the results of MTT assay according to Experiment Example 2.
Figure 4:
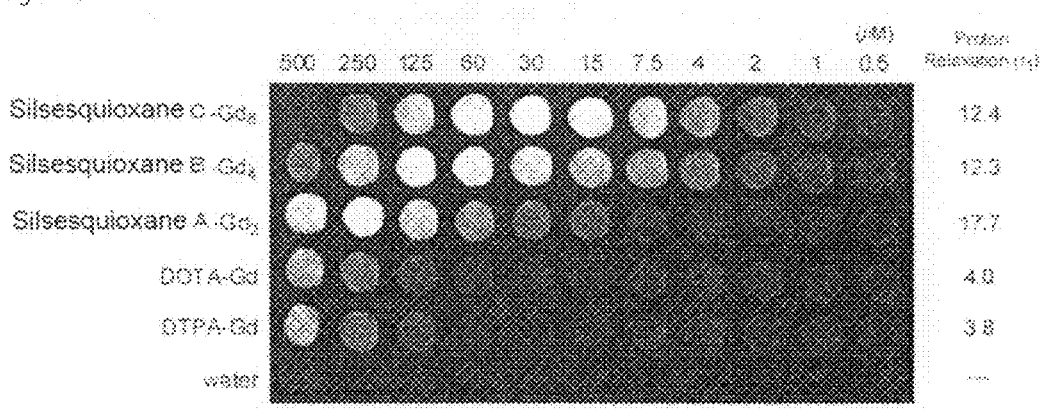
FIG. 4 is an MRI image in relation to Experiment Example 3. The horizontal axis denotes the ligand concentrations (μM) of the aqueous solutions, and the vertical axis denotes the metal complexes contained in the aqueous solutions.

The invention claimed is:

1. A contrast agent containing:

(A) a silsesquioxane represented by General Formula (I),

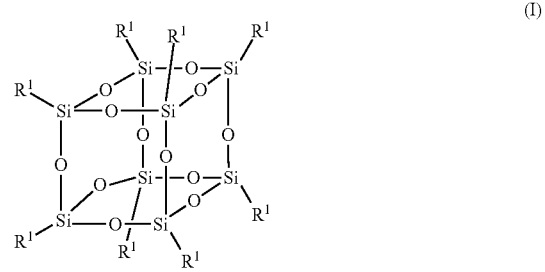

wherein $R_1$, the same or different, is a substituent bonded to Si through a carbon atom, the substituent having, at its terminal, a group represented by General Formula (II),

wherein p represents an integer of from 1 to 5, q is the same or different, and represents an integer of from 1 to 5, and $R^2$ is hydrogen atom, or a group represented by General Formula (III),

wherein p, q and $R^2$ are the same as above; and (B) a paramagnetic metal ion.

2. The contrast agent according to claim 1, wherein $R^1$ is a group represented by General Formula (IIA),

wherein p, q and $R^2$ are the same as above, or a group represented by General Formula (IIIA),

wherein p, q and $R^2$ are the same as above.

3. A contrast agent containing:

(A) a silsesquioxane represented by General Formula (I),

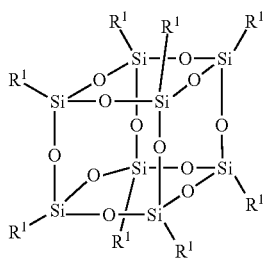

(I)

wherein $R^1$ is a substituent represented by General Formula (IIB),

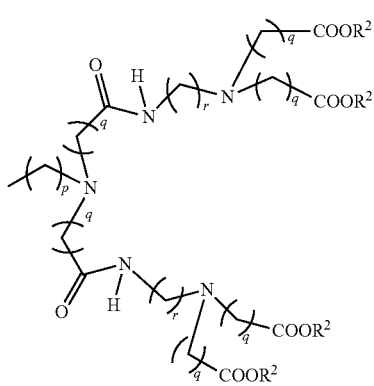

(IIB)

wherein p represents an integer of from 1 to 5, q is the same or different, and represents an integer of from 1 to 5, r is the same or different, and represents an integer of from 2 to 10, and $R^2$ is hydrogen atom; and (B) a paramagnetic metal ion.

4. A contrast agent containing:

(A) a silsesquioxane represented by General Formula (I),

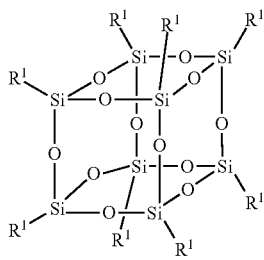

(I)

wherein $R^1$ is a substituent represented by General Formula (IIC),

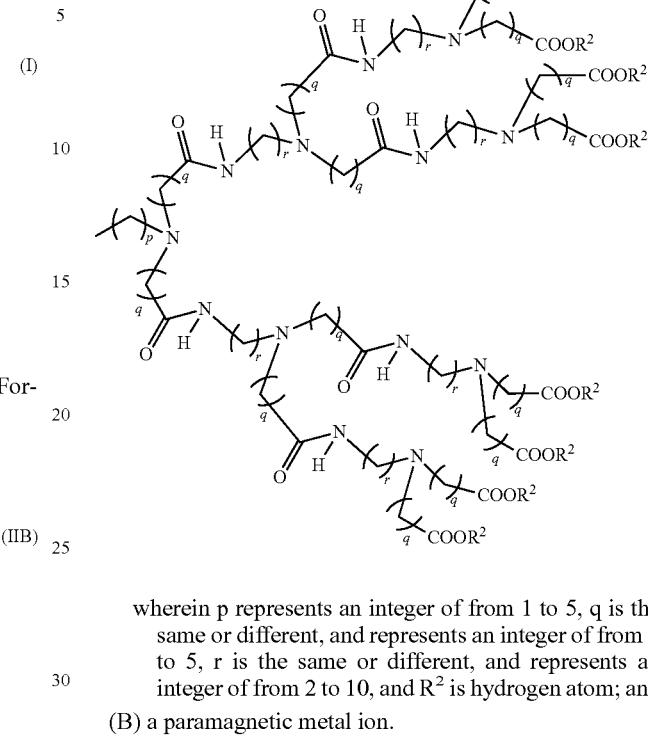

(IIC)

wherein p represents an integer of from 1 to 5, q is the same or different, and represents an integer of from 1 to 5, r is the same or different, and represents an integer of from 2 to 10, and $R^2$ is hydrogen atom; and (B) a paramagnetic metal ion.

5. The contrast agent according to claim 1, wherein the paramagnetic metal ion is $Gd^{3+}$.

6. The contrast agent according to claim 1, wherein the contrast agent is a contrast agent for MRI.

7. A silsesquioxane represented by General Formula (Ia),

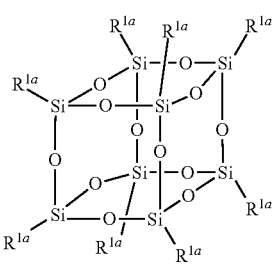

(Ia)

wherein $R^{1a}$, the same or different, is a substituent bonded to Si through a carbon atom, the substituent having $-N(-CH_2-COOH)_2$ or $-NH-CH_2-COOH$ at its terminal.

8. The silsesquioxane according to claim 7, wherein the $R^{1a}$ is a substituent represented by General Formula (IIa),

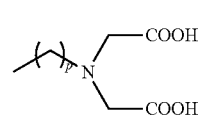

(IIa)

wherein, p is an integer of from 1 to 5, or a group represented by General Formula (IIIa),

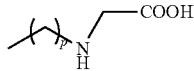
(IIIa)

wherein p is the same as above.

9. A silsesquioxane represented by General Formula (Ia),

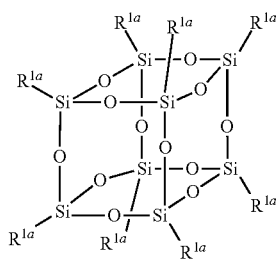
(Ia)

wherein $R^{1a}$ is a substituent represented by General Formula (IIb),

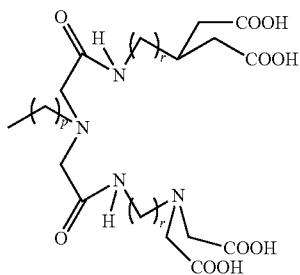
(IIb)

wherein p is an integer of from 1 to 5, and r is the same or different, and is an integer of from 2 to 10.

10. A silsesquioxane represented by General Formula (Ia),

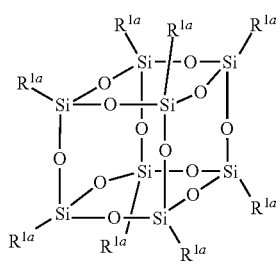
(Ia)

wherein the $R^{1a}$ a is a substituent represented by General Formula (IIc),

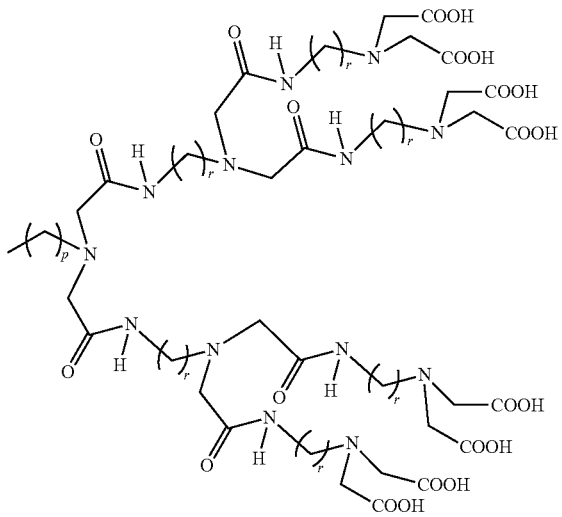
(IIc)

wherein p is an integer of from 1 to 5, and r is the same or different, and is an integer of from 2 to 10.

11. A silsesquioxane metal complex wherein the silsesquioxane according to claim 7 is coordinated to a metal ion.

12. A process for producing a silsesquioxane represented by General Formula (I2),

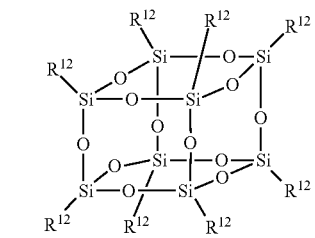
(I2)

wherein $R^{12}$, the same or different, is a substituent bonded to Si through a carbon atom, the substituent having, at its terminal, a group represented by General Formula (II2),

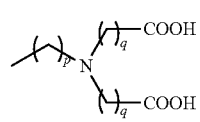
(II2)

wherein p is an integer of from 1 to 5, and q is the same or different, and is an integer of from 1 to 5, or a group represented by General Formula (III2),

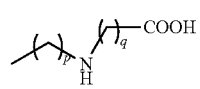
(III2)

wherein p and q are the same as above,
the process comprising the steps of:
(1) reacting an amino compound or its salt represented by General Formula (IV),

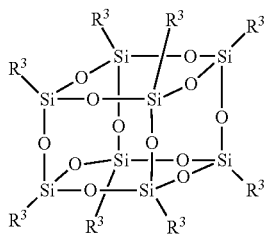

(IV)

wherein $R^3$, the same or different, is a substituent bonded to Si through a carbon atom, the substituent having $-(CH_2)_p-NH_2$, wherein p is the same as above, at its terminal, with an ester compound represented by General Formula (V),

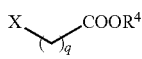

(V)

wherein $R^4$ represents alkyl group, aralkyl group or acyl group, X represents Cl, Br or I, and q is the same as above, thereby obtaining a silsesquioxane represented by General Formula (I1),

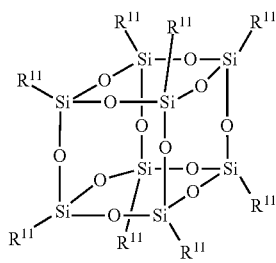

(I1)

wherein $R^{11}$ is the same or different, and is a substituent having, at its terminal,

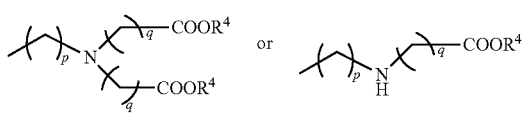

wherein p, q and $R^4$ are the same as above; and (2) converting the $R^4$ of the silsesquioxane (I1) obtained in Step (1) into a hydrogen atom.

13. The process according to claim 12, for producing a silsesquioxane represented by General Formula (IA2),

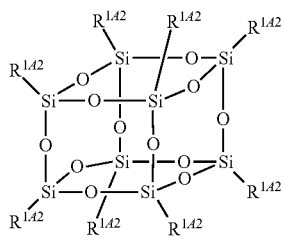

(IA2)

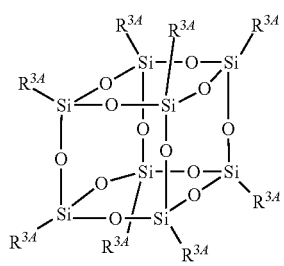

wherein p and q are the same as above, and $R^{IA2}$ is the same or different, the process comprising the steps of:

(1) reacting an amino compound or its salt represented by General Formula (IVA),

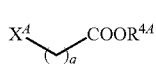

(IVA)

wherein $R^{3A}$ is the same or different, and represents $-(CH_2)_p-NH_2$, wherein p is the same as above, with an ester compound represented by General Formula (VA), $$X^A \diagdown_{()_q} COOR^{4A}$$ (VA)

wherein $R^{4A}$ represents alkyl group, aralkyl group or acyl group, $X^A$ represents Cl, Br or I, and q is the same as above;

thereby obtaining a silsesquioxane represented by General Formula (IA1),

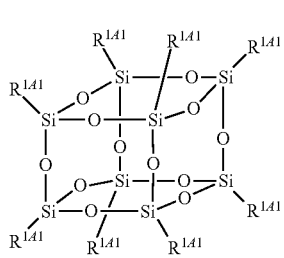

(IA1)

-continued

wherein p, q and $R^{4A}$ are the same as above, and $R^{IA1}$ is the same or different; and (2) converting the $R^{4A}$ of silsesquioxane (IA 1) obtained in Step (1) into a hydrogen atom.

14. A process for producing a silsesquioxane represented by General Formula (IB2), (IB2)

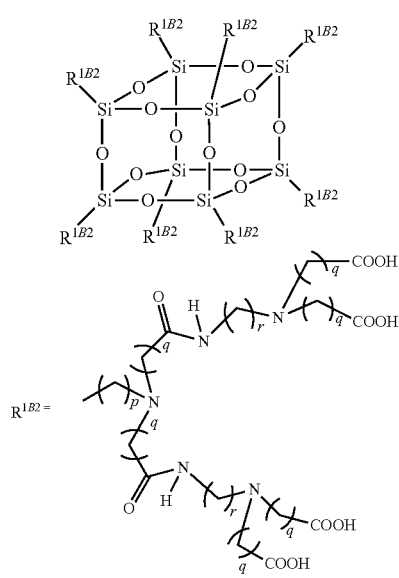

wherein p is an integer of from 1 to 5, q is the same or different, and is an integer of from 1 to 5, r is the same or different, and is an integer of from 2 to 10, and $R^{IB2}$ is the same or different, the process comprising the steps of:

(1) reacting an amino compound or its salt represented by General Formula (IVA), (IVA)

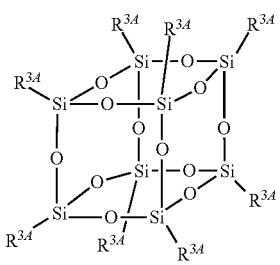

wherein $R^{3A}$ is the same or different, and represents —$(CH_2)_p$—$NH_2$, wherein p is the same as above, with an ester compound represented by General Formula (VB1),

(VB1)

wherein $R^{4B1}$ represents alkyl group, aralkyl group or acyl group, $X^{B1}$ represents Cl, Br or I, and q is the same as above, thereby obtaining a silsesquioxane represented by General Formula (IB1), (IB1)

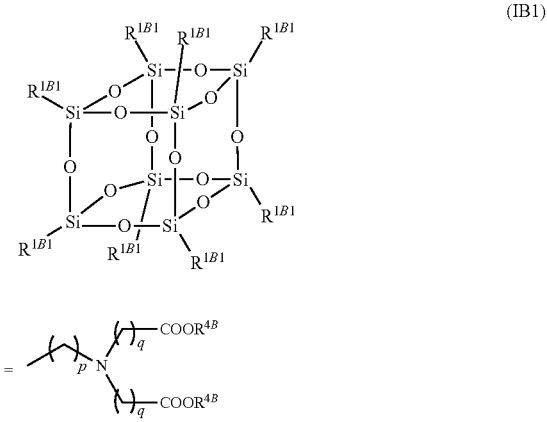

wherein p, q and $R^{4B}$ are the same as above;

(2) reacting the silsesquioxane (IB1) obtained in Step (1) with a diamine compound represented by General Formula (VIB),

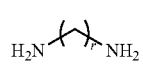
(VIB)

wherein r is the same as above, thereby obtaining an amide compound represented by General Formula (IVB), (IVB)

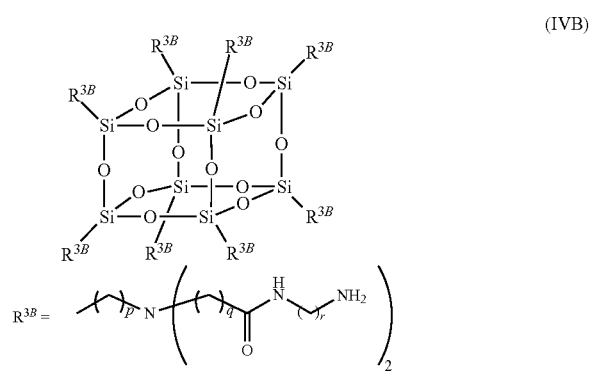

wherein p, q and r are the same as above, and $R^{3B}$ is the same or different;

(3) reacting the amide compound obtained in Step (2) with an ester compound represented by General Formula (VB2),

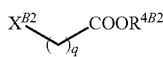
(VB2)

wherein $R^{4B2}$ represents alkyl group, aralkyl group or acyl group, $X^{B2}$ represents Cl, Br or I, and q is the same as above, thereby obtaining a silsesquioxane represented by General Formula (IB1')

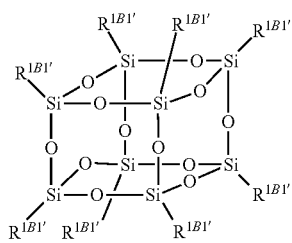
(IB1')

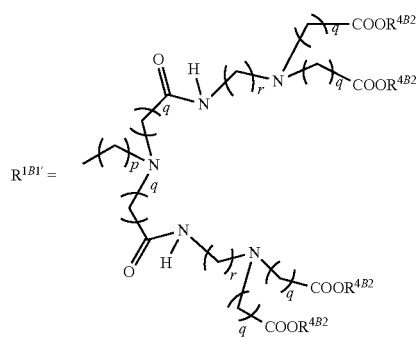

wherein p, q, and $R^{4B2}$ are the same as above, and $R^{IB1'}$ is the same or different; and (4) converting the $R^{4B2}$ of the silsesquioxane (IB1') obtained in Step (3) into a hydrogen atom.

15. A process for producing a silsesquioxane represented by General Formula (IC2),

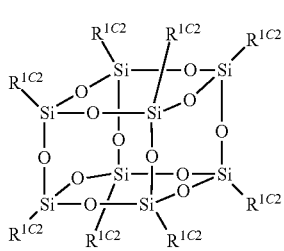
(IC2)

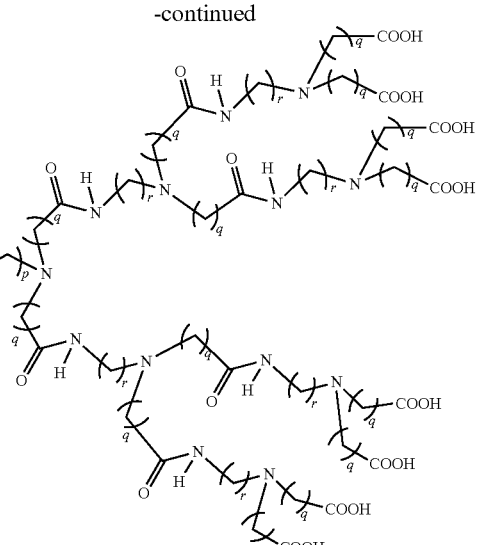

wherein p is an integer of from 1 to 5, q is the same or different, and is an integer of from 1 to 5, and r is the same or different, and is an integer of from 2 to 10, and $R^{Ic2}$ is the same or different, the process comprising the steps of:

(1) reacting a silsesquioxane represented by General Formula (IB1')

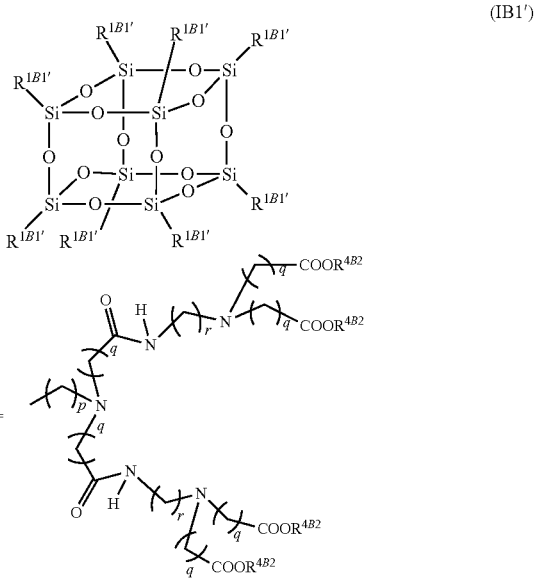
(IB1')

wherein p, q, and r are the same as above, and $R^{4B2}$ represents alkyl group, aralkyl group or acyl group, and $R^{IB1}$ is the same or different;

with a diamine compound represented by General Formula (VIC),

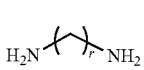
(VIC)

wherein r is the same as above,
thereby obtaining an amide compound represented by General Formula (IVC),

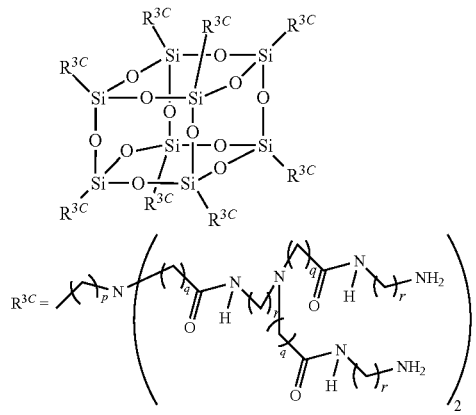
(IVC)

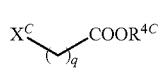

wherein p, q and r are the same as above, $R^{3C}$ is the same or different;
(2) reacting the amide compound obtained in Step (1) with an ester compound represented by General Formula (VC), $$X^C\underset{q}{\frown}COOR^{4C} \quad (VC)$$

wherein $X^C$ represents Cl, Br or I, $R^{4C}$ represents alkyl group, aralkyl group or acyl group, and q is the same as above, thereby obtaining a silsesquioxane represented by General Formula (IC 1),

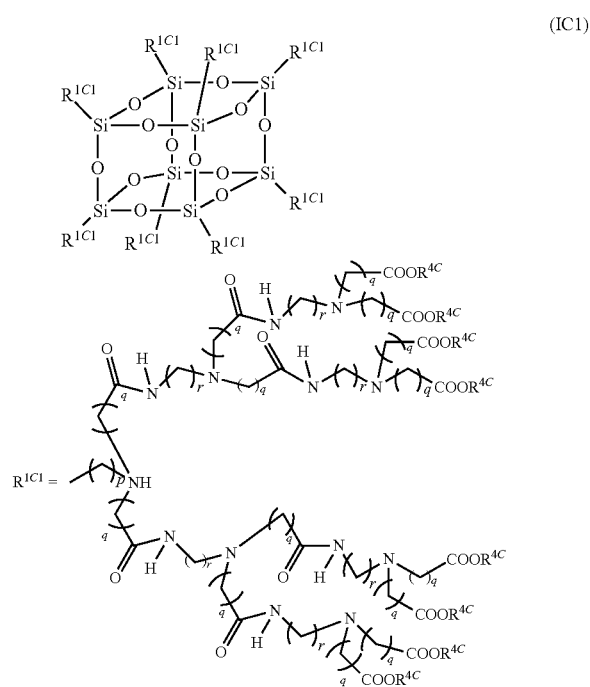
(IC1)

wherein p, q, r and $R^{4C}$ are the same as above, and $R^{Ic1}$ is the same or different; and
(3) converting the $R^{4C}$ of the silsesquioxane (IC1) obtained in Step (2) into a hydrogen atom.

* * * * *